United States Patent [19]

Cabezas

[11] Patent Number: 5,176,912
[45] Date of Patent: Jan. 5, 1993

[54] METHOD OF TREATING PSORIASIS

[76] Inventor: Orestes Cabezas, 10201 Fountainbleau Blvd., #205, Miami, Fla. 33172

[21] Appl. No.: 647,245

[22] Filed: Jan. 29, 1991

[51] Int. Cl.⁵ .................. A61K 31/52; A61K 37/54
[52] U.S. Cl. .................. 424/94.63; 514/263; 514/264; 514/400; 514/863
[58] Field of Search ............ 514/263, 863, 264, 400; 424/94.63

[56] References Cited

U.S. PATENT DOCUMENTS

| | | | |
|---|---|---|---|
| 4,341,783 | 7/1982 | Scheindlin | 514/263 |
| 4,708,964 | 11/1987 | Allen | 514/263 X |
| 4,826,677 | 5/1989 | Mueller et al. | 514/863 X |

Primary Examiner—Leonard Schenkman
Attorney, Agent, or Firm—Malloy, Downey & Malloy

[57] ABSTRACT

A method of treating psoriasis which includes subcutaneously injecting into the tissue of a person a dose of cc of a mixture composed of 0.1 milligrams histamine phosphate, 9.25 milligrams bacteriologic peptadase, 110.00 milligrams diprophylline, 4.0 milligrams chlorophenamine, about 0.1 milligram methyl paraben and propylparaben, about 0.2 milligrams sodium chloride, water and then observing the site for between one and three days to observe when the tissue surface at the site is no longer inflamed and is normal and, then, successively injecting 1 cc again and again with a similar observation interval for a period of about two weeks to develop a tolerance to the mixture; and thereafter, repeating the process of injecting every twenty-four hours to seventy-two hours with a 2 cc injection until the symptoms of the psoriasis condition disappear.

5 Claims, No Drawings

METHOD OF TREATING PSORIASIS

BACKGROUND OF THE INVENTION

The present invention relates to a series of treatments for the dermatological condition accompanied by pathological cell proliferation.

Diseases accompanied by a pathological epidermal cell proliferation are relatively frequent and concern a substantial portion of the population. A main condition is known as psoriasis. Previous efforts to resolve symptoms of this disease include the method of U.S. Pat. No. 4,328,231 which teaches a topical application to the skin of a person with the disease; the method of U.S. Pat. No. 4,228,176, wherein a patient is administered an anti-inflammatory amount of Burimamide or a pharmaceutically acceptable salt thereof; the method of U.S. Pat. No. 3,212,970, wherein an antihistaminic component is utilized and injected intramuscularly; and the method of U.S. Pat. No. 3,904,766, wherein tolerance is induced to the drug, mechlorethamine hydrochloride, by intravenous injections over a three week period and, subsequently and periodically applying topically a composition of the chemical in an anhydrous pharmaceutically acceptable carrier.

The present invention is of the discovery that a patient having the disease of psoriasis may enjoy a disappearance of the symptoms by, first, building a tolerance by subcutaneous injections of a medicine described below during a period of about two weeks with the successive injections spaced from one another by a period of about one to three days. The medicine is a solution sold under the commercial name Desensil. After the two week period of successive injections and the development of tolerance, the amount of the injections is increased from one cc to no more than two cc's per injection and the process is continued until the symptoms of the psoriasis condition disappear.

Numerous patients have been treated in accordance with this method with the result that the symptoms of psoriasis disappear and, in some cases, do not return at all, and in other cases, symptoms subsequently return, usually during or after a period of stress which has been undergone by the patient.

In a first example, the Desensil was injected for a period of fifteen days in an amount of 1 cc per injection. The first injection resulted in a small bulbous zone at the site of the injection which turned red and in a period of twenty-four hours subsided with the redness disappearing and the site assuming a normal appearance. The injections of 1 cc were continued each twenty-four hour interval during a period of fifteen days. During this period a clinical chart of the process was maintained. At the end of the two week period and the development of tolerance, the injections were increased to two cc's every other day for a period of sixty days. During the two month period, a gradual reduction in the symptoms of psoriasis was noted and at the end of the two month period, the symptoms had disappeared entirely.

In another example, the same process was repeated wherein the period for the development of the tolerance was maintained at about two weeks or fourteen days; however, it was noted that the skin following the 1 cc injection did not return to normal for a period of about forty-eight hours after each injection. After the two weeks initial tolerance developing period, the 2 cc's injections were commenced and after a period of six months during which the symptoms gradually diminished, all of the symptoms had disappeared.

In a third example, after initial tolerance injections for a two week period, the 2 cc injections were periodically applied for four months; and it was found that the 1 cc injections during the tolerance building two week initial period required almost three days for the skin at the site of the injection to return to normal. During the four month period, the symptoms gradually disappeared.

The Denesil solution is available from the Minister of Health, Public Pharmaceutical Laboratory, JULIO TRIGO, Calzada de Boyeros, km 7½, Boyeros, Cuba. That mixture is composed in each milliletor of 0.1 milligrams histamine phosphate, 9.25 milligrams bacteriologic peptadase, 110.00 milligrams diprophylline, 4.0 milligrams chlorophenamine, about 0.1 milligram methyl terabine propylparaben, about 0.2 milligrams sodium chloride, and water. The amount of the latter two ingredients and the water may be varied with respect to one another and preferably distilled water is used.

This solution must be maintained in a cool condition and, since it is sensitive to light, in an opaque container. The medicine was developed for the treat of allergies; but no specific use was assigned to it. It has been discovered that this solution utilized in the manner described herein causes the symptoms of psoriasis to disappear. Once the symptoms disappear, it has been observed that on several occasions, the psoriasis condition reappeared. This happened when the person was under stress. In those relatively few cases, a repeating of the method described herein, once again, caused the symptoms to disappear.

The subcutaneously injected mixture of solution is injected into the tissue, and not into the blood. The skin turns red at the site of the injection; and a small bulbous protrusion can be observed. The redness, however, disappears and the appearance of the skin at the injection site returns to normal within a week and usually within twenty-four to forty-eight hours. When the redness or the skin returns to a normal appearance, the injection is repeated again in the initial tolerance building process, and, thereafter, in the 2 cc treatment injections until the psoriasis symptoms disappear. The injections are not deep but rather just beneath the surface of the skin and at the injection site there appears to be a little bubble under the skin for a period of one or two days while the solution is absorbed.

While this invention has been shown and described in what is considered to be a practical and preferred embodiment, it is recognized that departures may be made within the spirit and scope of this process which should therefore not be limited except as set forth in the claims which follow hereinafter within the doctrine of equivalents.

What is claimed is:

1. The method of treating psoriasis comprising the steps of:
    a) first injecting subcutaneously in the tissue of a person at a site on the person one cc of a mixture, said mixture comprising per millimeter:
        0.1 milligrams histamine phosphate
        9.25 milligrams bacteriologic peptadase
        110.00 milligrams diprophylline
        4.0 milligrams chlorophenamine
        about 0.1 milligram methyl paraben and propylparaben about 0.2 milligrams sodium chloride Water;

b) second, when the tissue surface at the site is no longer inflamed and is normal, inject 1 cc again;

c) third, repeat the second step of this process for a period to develop tolerance to the mixture;

d) fourth, after the period of about two weeks to develop tolerance, inject no more that 2 cc's per injection until the symptoms of the psoriasis condition disappear.

2. The method of claim 1 wherein 2 cc's are injected per injection in performing the fourth step.

3. The method of claim 1 wherein the site is on the inside forearm of the person.

4. The method of claim 1 wherein the period of the third step is at least two weeks.

5. The method of claim 3 wherein the period of the third step is at least two weeks.

* * * * *